United States Patent [19]

Ley

[11] Patent Number: 4,669,643

[45] Date of Patent: Jun. 2, 1987

[54] ELECTRONIC LARYNX CARRIER

[75] Inventor: Carl Ley, Honolulu, Hi.

[73] Assignee: Linda E. Hymes, Hinsdale, Ill.

[21] Appl. No.: 841,953

[22] Filed: Mar. 20, 1986

[51] Int. Cl.⁴ ............................................. A45F 3/14
[52] U.S. Cl. ................................... 224/257; 224/202; 381/70; 623/9
[58] Field of Search ............... 224/257, 258, 202, 205, 224/148; 381/70; 623/9

[56] References Cited

U.S. PATENT DOCUMENTS

| | | | |
|---|---|---|---|
| 4,028,492 | 6/1977 | Sickel | 381/70 |
| 4,292,472 | 9/1981 | Lennox | 381/70 |
| 4,347,956 | 9/1982 | Berger | 224/202 |

Primary Examiner—Stephen Marcus
Assistant Examiner—David Voorhees
Attorney, Agent, or Firm—Hill, Van Santen, Steadman & Simpson

[57] ABSTRACT

A carrier for supporting an electronic larynx adjacent portions of the throat of a user so that muscles of the user can be employed to switch on and off the larynx without manual action. The carrier employs a base plate to which are mounted an interfacing plate member on the inside face and a formed sheet member on the outside face. An extension on the interfacing plate member engages the plunger switch of the electronic larynx which switch extends through a cutout formed in the base plate. The formed sheet member provides a pocket for receiving and holding the electronic larynx.

9 Claims, 5 Drawing Figures

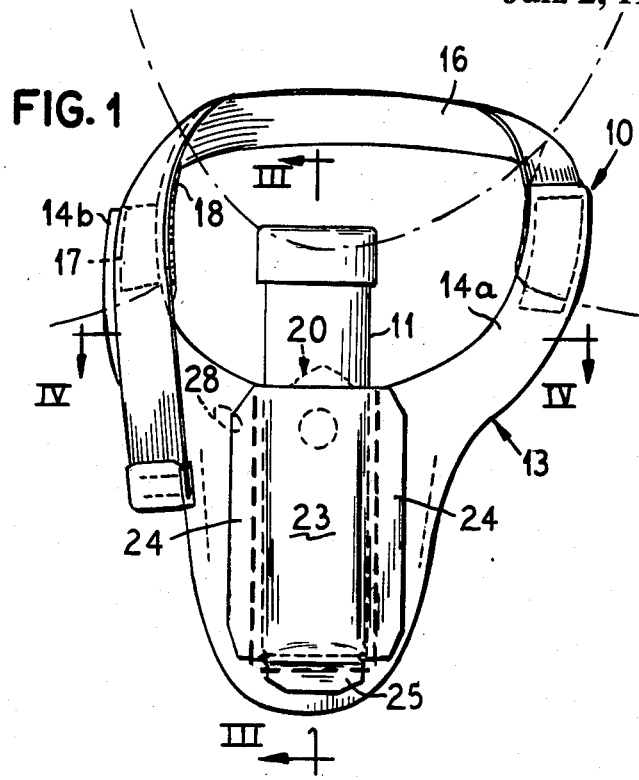
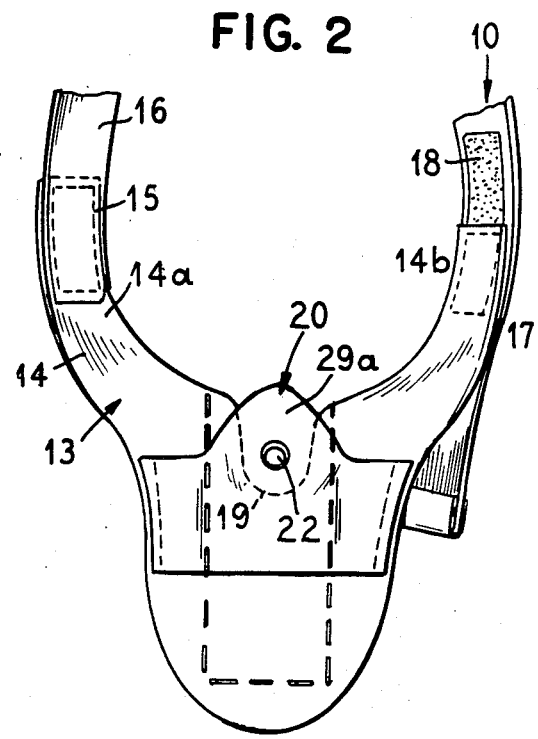
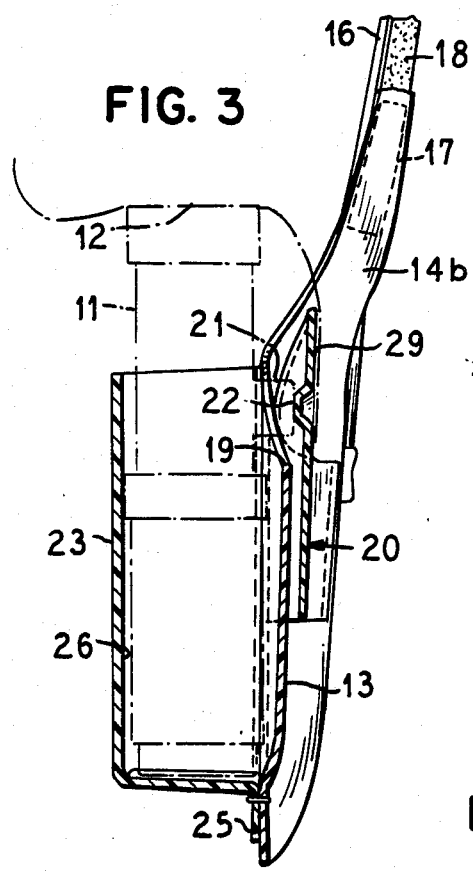
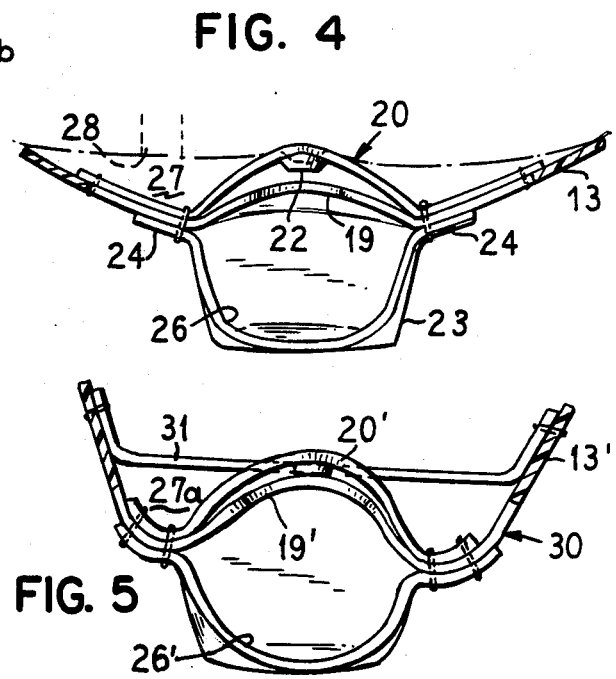

ELECTRONIC LARYNX CARRIER

BACKGROUND OF THE INVENTION

1. Field of the Invention

This invention lies in the field of carriers for electronic larynxes, and, more particularly, of such carriers which permit self-actuation and de-actuation by a user.

2. Description of the Prior Art

Neck associated devices by which a user generates electronically produced sound have in recent years been commercially available and have come into general use by persons who have undergone a laryngectomy.

Typically, a hand held electronic larynx resembles a foreshortened two-battery flashlight. The forward end is provided with a disk-like member which, when activated, vibrates with a buzzing sound. In the prior art, the user manually places the disk end on his neck and presses a button associated with the device to start or to stop transducer-induced vibration of the disk member. This vibration is transmitted through the soft tissue of the throat and into the oral cavity for the tongue, lips, and teeth to articulate words as one does with vibration from the larynx (or vocal cords). The result is the production of sound modulated with the words generated by the user.

With the larynx gone, the trachea needs direct access to air, so during larynx removal, the surgeon cuts a hole (a stoma) just above the base of the neck and sews the edges of the trachea to it. The patient breathes through the stoma for the rest of his life. The stoma is kept open with a metal tracheostomy tube for several weeks until the tissue around its edges heals. One continuing problem is the need to periodically clear the tracheostomy tube by a suction machine, sometimes for several weeks following the initial surgery. The tracheostomy tube consists of a pair of telescopically inter-engaged tube members with the outer tube being secured by a latch. Any carrier device for an electronic larynx cannot interfere with the breathing capabilities of the stoma.

Esophageal speech is the goal of most laryngectomees, but even skilled speakers rely on an artificial electronic larynx most of the time, particularly when speaking in an noisy place, or when they are tired or have a cold. Esophageal speaking is a process of swallowing air (charging) held in the esophagus and then releasing it like a belch from talking deep in the throat (akin to gargling). The vibrating esophagus makes the sound which is articulated and formed into words by the lips, tongue, and teeth. Because of the problems involved, most patients evidently prefer an electronic larynx device for general speech purposes. Auxiliary device supporting structures aid a user and facilitate employment thereof.

So far as is known, no carrier for an electronic larynx device of the hand hold type has been previously known to the prior art whereby such a hand holdable electronic larynx device is held and positioned by the carrier in an operative position and association with the neck and jaw region of a user.

BRIEF SUMMARY OF THE INVENTION

More particularly, this invention relates to a new and very useful carrier for an electronic larynx device which carrier enables the user to hold and position such device against his neck at the base of his jaw, so that by inducing muscle contractions, the user can activate the on/off switch associated with such device, thereby enabling the user to turn on the device just before speech is commenced and then to turn off the device just after speech has terminated, such switch actuation being accomplished by no manual intervention.

An object of this invention is to provide a carrier device which will enable one to utilize without manual involvement once the carrier device is in place a conventional, commercially available electronic larynx of the type adapted for hand held usage.

Another object is to provide a carrier apparatus for an electronic larynx which permits the user of such apparatus to actuate and de-actuate by muscle action only, originating in the neck and throat region, thereby to free the hands of the user from holding such device and from requiring hand actuation of the on/off switch associated with the device, and thereby also to achieve a maximized efficient usage of the battery in the device for obtaining a maximized battery life.

Another object is to provide, in a carrier apparatus, a mounting arrangement for holding and positioning the carrier apparatus in the neck region adjacent to the base of the throat, and which also permits an infinitely variable adjustment of mounting positions for the carrier apparatus, both for the convenience of a user, and for permitting a given carrier apparatus construction to be employable for usage with a wide variety of individual users, each of whom may have differences in his external anatomy in the general region of carrier assembly location and usage.

Another object is to provide in a carrier apparatus of the class above indicated a simple, reliable, durable construction which is easy to mount in and de-mount from, an operative association about a user's neck.

Another object is to provide a carrier apparatus of the class indicated which can, with relatively minor variations or modifications, be employed with various different electronic larynx devices.

Another object is to provide a carrier apparatus for an electronic larynx which apparatus does not interfere with the ability of a user to accomplish breathing through his stoma.

Another object is to provide a carrier for an electronic larynx which can be rapidly and safely positioned and removed from the neck region of a user.

Other and further objects, aims, purposes, features, advantages, and the like will be apparent to those skilled in the art from the teachings of the present specification taken with the accompanying drawings.

BRIEF DESCRIPTION OF DRAWINGS

In the drawings:

FIG. 1 is a front elevational view of one embodiment of an electronic larynx carrier of the present invention;

FIG. 2 is a fragmentary rear elevational view of the embodiment shown in FIG. 1;

FIG. 3 is a vertical sectional view taken along the line III—III of FIG. 1;

FIG. 4 is a horizontal sectional view taken along the line IV—IV of FIG. 1; and

FIG. 5 is a view similar to FIG. 4, but showing an alternative embodiment of the present invention.

DETAILED DESCRIPTION

Referring to the drawings (FIGS. 1-4), there is seen an embodiment of an electronic larynx carrier which is herein designated in its entirety by the numeral 10. The carrier 10 is adapted to hold a specific user-chosen type of electronic larynx, which here is generally referred to by the numeral 11, against a portion of the throat located at the base of the chin of an individual using an electronic larynx. Electronic larynx structures particularly of the hand held type are known to the prior art and are available commercially; they do not as such comprise a point of novelty in the present invention. The carrier 10 functions to hold the electronic larynx 11 in an operable position against such throat portion, and the carrier 10 permits the user to turn the electronic larynx 11 on before speech is attempted, and then off, following completion of speech, without manual action.

The carrier 10 is generally comprised of coacting associated rigid preformed plastic sheet members, Teflon being a presently preferred material of construction for such sheet members. Thus, the carrier 10 employs a base plate 13 which can be constructed, for example, of Teflon sheeting of approximately 1/16th inch thickness. The base plate 13 can have side and bottom portions configured as desired and the top portion is configured to include supporting means for positioning carrier 10 in a desired location in relation to the needs of a user. For example, a pair of symmetrical, transversely spaced, integrally formed, upstanding side extensions 14.

One of such side extension identified as 14a serves as a base leg against one side of which a flexible strap or fabric web 16 is associated by fastening means, such as stitching 15, or the like, as desired. The web 16 is adapted to extend upwards from extension 14a and around the back of the neck of the user and then down into overlapping adjacent relationship with the other side extension 14b. Mating Velcro strips 17 and 18 are provided, the strip 17 being associated by fastening means, such as stitching, or the like, with the outside face of extension of 14b, and the strip 18 being associated similarly with adjacent inside face portions of the web 16, thereby permitting an interlocking but disengageable engagement of the web 16 to occur with respect to the extension 14b by means of inter engagement of the surfaces of the Velcro strips 17 and 18. The Velcro strips 17 and 18 permit the web to be infinitely adjusted so as to achieve small incremental changes in the position and location of the carrier 10 thereby to permit a user to achieve an exact optimum location desired by him for his larynx 11. Thus, a given carrier 10 can be used for an indefinitely large number of individuals who may differ from one another in such matters as neck size, stoma location, etc.

Centrally, in the upper perimeter of base plate 13, and approximately midway between the respective side extensions 14, a cutout 19 is provided. This cutout 19 is sized and located so as to permit the on/off plunger switch 21 of the larynx 11, which switch is pressure actuatable and is of the plunger type, to project into and through the cutout 19, as shown.

An interfacing plate member 20 is provided which, in effect, is interposed between such projecting switch 21 and an adjacent surface portion of the neck of the user. Conveniently, and as shown in the embodiment shown, opposed lateral side edges of the plate member 20 extend beyond the cutout 19 and are secured to adjacent portions of the base plate 13 by fastening means, such as stitching, or the like. The central region 29 of the interfacing plate member 20 is cylindrically curved so as to be raised relative to the adjacent transversely spaced portions of the base plate 13. The upper central region 29a of plate member 20 projects upwards relative to the main body thereof. The projection 29a provides desirable flexibility and also facilitates achievement of a desired overlying relationship between the projecting portion 29a of the plate member 20 and the cutout 19. The projection 29a provides a yielding bias action, thereby providing the capability for spring-like flexural or pivoted movements particularly of uppermost tip portions thereof towards and away from the adjacent surface portions of the user's neck, which is desirable when the user is achieving switching action of (that is, turning on or off) the electronic larynx 11.

Optionally, but preferably, a raised button region 22 is provided in the base region of the projection 29a of the interfacing plate member 20. This button region 22 is raised in the surface of projection 29a and the button region 22 extends in the direction of the switch 21. The button region 22 functions to provide selective contact with end portions of the switch 21, thereby to enhance sensitivity for on and off actuation movements of the switch 21.

In order to provide a holding chamber 26 for supporting the typically cylindrically shaped electronic larynx 11, a pocket-shaped sheet member 23 is mounted on the front face of the base plate 13. In the embodiment shown, the sheet member 23 is provided with opposed side flanges 24 and with a base flange 25, which flanges are each conveniently secured to associated underlying portions of the base plate 13 by fastening means, such as stitching, or the like, as desired. Thus, a combination of the sheet member 23 and of the base plate 13 coact to provide the pocket-like receiving or holding chamber 26, whose dimensions are such as to permit receipt thereinto by loose sliding engagement of the main body portion of the electronic larynx 11. It is preferred to employ a continuous member for sheet 23 to minimize clothing entanglements or the like in the vicinity if the neck for user.

Another function for the cutout 19 is now seen which is to provide a key way for orienting the electronic larynx 11 in a fixed position, the keying being accomplished by locating the switch 21 in a relatively fixed relationship to the side edges of the cutout 19 when the larynx 11 is positioned in chamber 26.

The radius of curvature of the base plate 13 (and also the opposite radius of the plate member 20) are such as to produce and maintain a vertically extending air passage 27 between the user's neck in the region of the carrier and of the stoma 28.

Referring to FIG. 5 and the alternative carrier embodiment thereshown, it is seen that the carrier of FIG. 5 (which is herein designated in its entirety by the numeral 30) has a greater radius of curvature along the opposed lateral side portions of the chamber 26' than is present in carrier 10. A retaining strap 31 of Teflon or the like extends transversely between lateral side portions of the base plate 13' and is secured at its opposed ends by stitching or the like to plate 13 is provided in order to reinforce and stabilize the configuration shown. The components in the carrier embodiment 30 which are similar to corresponding components in the carrier embodiment 10 are similarly numbered, but with the addition of prime marks thereto.

Proportions, dimensions, and similar matters are regulatable as desired in an embodiment of carrier 10 or 30 in order to enhance adaptation of a given carrier for a given user or for employment of a particular electronic larynx device in combination with a particular carrier embodiment of this invention.

The physical contours of each person vary. As those skilled in the art will appreciate, when, for example, the carrier 10 is comprised of pieces of Teflon sheeting, the initial shape of the individual sheeting curvatures can be altered by heating slightly and molding portions of the unit, such as the base plate 13, before it cools, using manual pressures. In general, the horizontal location and the vertical pressure are critical adjustments in order for a given electronic larynx to function in association with a particular user. The horizontal location and the vertical pressure are adjustable by the webbing strip 16 in combination with the Velcro strips 17 and 18.

When the user nods his head, leverage is applied, allowing the top portion of the interfacing plate member 20 to transversely move relative to the adjacent neck of the user in a pivot type of action. Commonly, the interfacing plate member 20 may have to be slightly modified for optimum fitting in relation to individual user. Vertical pressure of the electronic larynx against the bottom of the chin and the tongue muscle allows actuation of the switch when the user's head is depressed.

The stitching employed with Teflon components in, for example, carrier 10 can be comprised of nylon thread.

If an electronic larynx should buzz when not in use, then its carrier can be warmed, grasped at its side seams, as with the left hand, and pressure exerted thereon by squeezing the fingers together and pressing down very gently until the interfacing plate member 20 is just clear of the electronic larynx switch.

Preferably, the desired configuration is held until the Teflon cools.

The electronic larynx 11 in a carrier 10 can be worn on either side of the stoma 28, depending on the location thereof in reference to the center line of the user's neck and the location of the vibrator head of the electronic larynx 11 against the throat needed in order to achieve a functional with relationship.

One convenient procedure for utilizing a carrier 10 is as follows:

1. The electronic larynx 11 is placed in the carrier 10.
2. The neck web 16 is adjusted around the neck of the user until the user feels familiar with the electronic larynx 10 on his or her neck. Such a familiarization procedure may extend over a period of half a day or so, if desired. When the carrier 10 is found comfortable, then the neck webbing 16 is adjusted so that the vibrator head of the electronic larynx 11 is just below the muscle at the base of the tongue, between the neck muscles of the cavity where the user's larynx was removed. The user preferably gently nods his head to activate the electronic larynx switch 21. However, as the user becomes familiar with the characteristics of the carrier 10 and, assuming the electronic larynx 11 is in a suitable location, the user learns to activate the switch 21 by merely flexing the muscle of his tongue.
3. A slight jerk of the end of the web 16 releases the carrier 10, thereby to permit, if desired, removal of mucus and to clean the stoma 28. The carrier 10 can, if desired, when formed of Teflon, be dipped into warm, soapy water, rinsed, and dried before reuse.

An electronic larynx 11 in a carrier 10 is preferably not worn during sleep, during athletic activities, or for unnecessary prolonged periods.

As can be appreciated from the foregoing description and accompanying drawings, every contour of the carrier 10 is purposeful.

Sometimes a user wishes to modify the length of the sensor switch 21 in relation to the vibrator cap at the forward end of an electronic larynx 11. The cavity above the stoma is a key factor. The depth of the cavity can vary. Also, some people have an oblong neck due to radiation damage in medical treatment, but such variations can be compensated for by adjustments in the carrier 10 by increasing, for example, the radius of curvature of the base plate 13, then the stoma can be cleared. If the neck is oblong, then the contour of the neck webbing can be used for compensation.

Of the base plate 13 is longer than the other side, preferably, for the purpose of placing and locating the electronic larynx 11 so that it will fit under the chin and into the neck cavity without obstructing the stoma. Locating of stitching can also be used to achieve variations in the interrelationships between component of a carrier 10. Modification of a sensor switch 21 may be accomplished by cutting a slight slant on each side of the switch in portions of the carrier 10. Also, the carrier 10 can be made longer at the bottom and narrower at the top, to give a more rounded contour, and such configuration will then provide more pressure with which to make on/off switching take place. Variations in pressure can be achieved by not incorporating a slant and by sewing the structure in a straight manner.

Commonly, a hand held electronic larynx 11 is equipped with a lanyard as a safety factor so that the user will not drop his device. Conveniently, the lanyard is left associated with the larynx 11 when same is mounted in a carrier 10.

The embodiment shown in FIGS. 1–4 is suitable for use with the Aurex "Neovox" "Electro-larynx" electronic larynx, which is available commercially from the Aurex Corporation, 337 South Franklin St., Chicago, Ill. 60606. This device is understood to include a screw cap adjustment for pitch which can be locked into the tone or speech sound the user prefers. Power is from a single rechargeable nickel-cadmium battery (two are included with each kit purchase together with a battery recharger). There are two models, the M520T, the male voice and the M520T-wm, the female voice. The latter is reportedly different in being pitched slightly higher and being softer-voiced and less powerful.

Another commercially available electronic larynx is the "Servox" from the Audiophone Company of South Texas, 201 Majestic Building, San Antonio, Tex. 78205.

Those skilled in the art will appreciate that, while Teflon (polytetrafluoroethylene) plastic sheeting is the presently preferred class of construction material, other plastics, especially thermoplastic resin can be used which are selected from among described, for example, in Modern Plastics Encyclopedia (1984–85) Vol 61 No. 10A. Obviously, thermally stable, non-skin irritating types are preferred.

While the carrier constructions described and illustrated herein are each formed of a plurality of discrete, separately pre-cut and preferably shaped sheet-like members, those skilled in the art will appreciate that a carrier construction of this invention can be readily and simply formed by injection or other plastic molding prcedure wherein a fiven carrier construction of the invention is conveniently and efficiently made in one piece with all plate and sheet members being integrally formed together, or wherein a given carrier construction of this invention is similarly made in two pieces. In the two piece procedure, the plate 20 is separately formed from the plate 13/sheet 23 combination and then the mating portions are secured together by adhesive, some welding, or the like. The bottom 22 can be produced in a post-welding forming operation. The web 16 is preferably separately affixed to a carrier extension 14a. The pocket 26 can be suspended from the base plate 13.

Having now fully described the invention, it will be apparent to one of ordinary skill in the art that many changes and modifications can be made thereto without departing from the spirit or scope of the invention as set forth herein.

I claim:

1. A carrier for an electronic larynx comprising in combination:
 a. a base plate having curved a back face such that when said base plate is positioned over the neck of a user, it overlies the user's stoma,
 b. supporting means for positioning said carrier to a discrete location relating to the neck of the user,
 c. a cutout region defined in an upper portion of said base plate and extending downwardly from the top center region thereof midway between a pair of extensions, said cutout region being adapted to receive therethrough the switch means of an electronic larynx,
 d. an interfacing plate member positioned centrally upon the back face of said base plate, and including fastening means mounting peripheral portions thereof to said base plate, said interfacing plate member including an upstanding central projection which generally overlies said cutout region having an opposed cylindrical curvature relative to that of said base plate whereby said interfacing plate member acts as a spacer for separating said base plate from a user's neck and whereby a vertically extending air space is defined on at least one side of said central projection, such air space being positioned to overlie the user's stoma, said upstanding central projection of said interfacing plate member being yieldingly, pivotably movable towards and away from a user's neck,
 e. a pocket means adapted for receiving slidably thereinto said electronic larynx with said switch thereof being positioned in said cutout region.

2. The carrier of claim 1 wherein said base plate, said interfacing plate member and said sheet member are comprised of Teflon.

3. The carrier of claim 1 wherein said base plate, said interfacing member and said sheet member are comprised of molded thermoplastic resin.

4. The carrier of claim 1 wherein a button region is centrally formed in said interfacing plate member and inwardly protrudes towards said cutout, said button region being adapted to engage said switch of said electronic larynx.

5. A carrier for positioning and mounting an electronic larynx which has an on/off switch adjacent the throat of a user so as to provide user on and off switching capability without manual action, a. a base plate having a length at least approximately the length of said electronic larynx, said base plate having a back face which generally cylindrically curved, the radius of curvature and the dimensions of said base plate being such that when said base plate is positioned over the neck of a user, and overlies the user's stoma,
 b. said base plate including a pair of integral upwardly extending side extensions, each one of such pair of extensions being located on an opposed upper side of said base plate,
 c. a flexible web member, one end thereof being secured to at least a portion of one of said extensions, the length of said web member being sufficient to extend around the neck of said user, the opposed end region of said web member being adapted to overlie at least a portion the other of said extensions, and said web member including fastening means for demountably and adjustably securing said opposed end region of said web member to a portion said other extention,
 d. a cutout region defined in an upper portion of said base plate and extending downwardly from the top center region thereof midway between said pair of extensions, said cutout region being adapted to receive therethrough the switch means of an electronic larynx,
 e. an interfacing plate member positioned centrally upon the back face of said base plate, and including fastening means mounting peripheral portions thereof to said base plate, said interfacing plate member including an upstanding central projection which generally overlies said cutout region having an opposed cylindrical curvature relative to that of said base plate whereby said interfacing plate member acts as a spacer for separating said base plate from a user's neck and whereby a vertically extending air space is defined on at least one side of said central projection, one such air space being positioned to overlie the user's stoma, said upstanding central projection of said interfacing plate member being yieldingly pivotably, movably towards and away from a user's neck, and
 f. a pocket adapted for receiving slidably thereinto said electronic larynx with said switch thereof being positioned in said cutout region.

6. The carrier of claim 1 wherein said base plate and integral side extensions, said interfacing plate member and said sheet member are comprised of Teflon and said fastening means which secures such members together comprises nylon stitchery.

7. The carrier of claim 1 wherein a button region is centrally formed and inwardly protrudes towards said cutout, said button region being adapted to engage said switch of said electronic larynx.

8. The carrier of claim 1 wherein said fastening means for demountably associating said web with said other extension comprises Velcro.

9. The carrier of claim 1 wherein a retaining strap is extended between inside opposed edge portions of said base plate and is secured thereto by fastening means thereby to retain a desired curvature in said base plate.

* * * * *